(12) United States Patent
Eberlein et al.

(10) Patent No.: US 8,388,665 B2
(45) Date of Patent: Mar. 5, 2013

(54) FASTENING ASSEMBLY

(75) Inventors: Roland Eberlein, Niederwürschnitz (DE); Lothar Wilberg, Bühleriann (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 908 days.

(21) Appl. No.: 11/804,572

(22) Filed: May 18, 2007

(65) Prior Publication Data

US 2008/0058817 A1 Mar. 6, 2008

Related U.S. Application Data

(60) Division of application No. 09/764,936, filed on Jan. 18, 2001, now Pat. No. 7,229,443, which is a continuation of application No. PCT/EP99/04973, filed on Jul. 14, 1999.

(30) Foreign Application Priority Data

Jul. 20, 1998 (DE) .................................. 198 32 513

(51) Int. Cl.
*A61B 17/80* (2006.01)
(52) U.S. Cl. ........................................ 606/290; 606/286
(58) Field of Classification Search .............. 606/70–71, 606/280–299
See application file for complete search history.

(56) References Cited

U.S. PATENT DOCUMENTS

| | | | |
|---|---|---|---|
| 4,038,801 A | 8/1977 | Busch | |
| 4,388,921 A * | 6/1983 | Sutter et al. | 606/71 |
| 4,971,497 A | 11/1990 | Stoffer et al. | |
| 5,053,036 A * | 10/1991 | Perren et al. | 606/291 |
| 5,057,111 A | 10/1991 | Park | |
| 5,269,784 A | 12/1993 | Mast | |
| 5,735,853 A * | 4/1998 | Olerud | 606/71 |
| RE36,164 E | 3/1999 | Johnson et al. | |
| 5,902,303 A * | 5/1999 | Eckhof et al. | 606/60 |
| 5,954,722 A * | 9/1999 | Bono | 606/281 |
| 7,311,712 B2 * | 12/2007 | Dalton | 606/71 |
| 2002/0082603 A1 | 6/2002 | Dixon et al. | |
| 2005/0192580 A1 * | 9/2005 | Dalton | 606/73 |

FOREIGN PATENT DOCUMENTS

| | | |
|---|---|---|
| DE | 3420 696 C1 | 10/1985 |
| DE | 297 01 099 U1 | 4/1997 |
| EP | 0 355 035 B1 | 5/1994 |
| EP | 0 809 975 A2 | 12/1997 |
| EP | 0 845 609 A1 | 6/1998 |
| GB | 2 305 483 A | 4/1997 |
| WO | WO 99/05968 | 2/1999 |

OTHER PUBLICATIONS

Translation of International Preliminary Examination Report; PCT/EP99/04973; Jul. 20, 2000.

* cited by examiner

*Primary Examiner* — Thomas Barrett
*Assistant Examiner* — Matthew Lawson
(74) *Attorney, Agent, or Firm* — Christie, Parker & Hale, LLP (57) ABSTRACT

A fastening assembly is provided for fastening a fixing element, for example a plate, a brace, an angle, a profile, an armature, a retainer or the like to a substructure by means of at least one screw, which can be passed through at least one bore in the fixing element and can be screwed into the substructure. A bushing is arranged in the bore to be able to be swiveled in arbitrary spacial direction. The screw is passed through the bushing. The bushing comprises a seat for at least partially receiving a head of the screw.

13 Claims, 4 Drawing Sheets

FASTENING ASSEMBLY

CROSS-REFERENCE TO RELATED APPLICATION(S)

This application is a divisional of allowed U.S. application Ser. No. 09/764,936, filed Jan. 18, 2001 now U.S. Pat. No. 7,229,443, which is a continuation of International Application PCT/EP99/04973 filed on Jul. 14, 1999, which designates the United States, and which claims priority to DE 198 32 513.4, filed Jul. 20, 1998, the entire contents of which are incorporated herein by reference.

BACKGROUND OF THE INVENTION

The invention relates to a fastening assembly for fastening a fixing element, for example a plate, brace, angle, profile, armature, retainer or the like, to a substructure by means of at least one screw which can be passed through at least one bore in the fixing element and can be screwed into the substructure.

Numerous fastening assemblies of the mentioned type are known, which are provided for many different types of applications.

For example, such fastening assemblies are used in the house-hold, for example to mount objects on the wall or ceiling, such as lamps, shelves or the like. Normally, fixing elements in the form of wall fixtures, profiles or the like are provided for such objects which must then be secured to the wall or the ceiling by means of one or more screws.

Such fixing elements normally have one or more bores through which a screw is passed and screwed into the substructure. In such cases, a hole is first drilled into the wall or the ceiling into which a dowel is inserted and the screw is then screwed into the dowel. By completely and firmly tightening the screw, the screw head forces the fixing element against the substructure.

Due to inexperience of the user in household applications or due to improper tools, it frequently occurs that the hole in the wall or the ceiling is not perpendicular to the surface, but is drilled at an angle. In particular, it is difficult to drill a perpendicular hole in the wall or ceiling when located close to a corner of the room, because the housing of the drilling machine makes it difficult or impossible to place the drill perpendicular to the ceiling or the wall.

If the hole in the wall or the ceiling is slanted, the screw must necessarily be screwed in at an angle through the bore in the fixing element and into the substructure. The shaft of the screw normally has a diameter which is only slightly smaller than the bore so that the shaft of the screw can clamp with the upper and/or lower edge of the bore. The screw can then only be applied with increased force exertion. In the worst case, it is not even possible to completely tighten down the screw and the fixing element is then not securely and immovably fixed to the substructure. This drawback can also not be avoided by an elongated configuration of the bore.

Even if the screw can be completely tightened and drawn down to the substructure, the screw head only contacts the edge of the bore. In the case of a countersunk screw, in some cases only a point contact is made with the fixing element. This does not ensure a solid play-free securement of the fixing element to the substructure.

Another application of such fastening assemblies is the do-it-yourself assembly of furniture, for example mounting hinges on cabinet doors or the like. In such cases, self-cutting wood screws are used as the screws. When mounting an angle, it is also frequently difficult to turn down the wood screws to be perpendicular to the cabinet wall because of the difficult access in the region of the angle. As soon as a few windings of the screw engage with the substructure, the orientation of the shaft with respect to the substructure and therefore with respect to the fixing element normally can not be corrected. The same problem then arises that the screws can not be completely tightened or only with excessive force to secure the fixing element immovably to the substructure.

A further important application of the mentioned fastening assembly lies in the medical field. Braces or splints are implanted in patients to heal bone fractures by fixing the broken bone portions, which are formed as elongated metal plates. At least two bores are provided in the brace, so that the brace can be applied across the fracture connecting the two bone portions. Bone screws are used as the screws, which are directly applied to the bones. Due the anatomical conditions of the patient or the location of bone fracture, it is also often necessary to apply the bone screws at an angle with respect to the bone brace. The same problem arises here as described above in conjunction with the technical applications.

In addition, for this application the bone parts to which the brace is to be secured do not have a flat uniform surface but have concave and convex undulations. In order to fix the brace immovably to the bone parts, the bone screw can not be screwed into the bone with excessive force. This would cause undesired tension or could even lead to an additional fracture of the bone. It is therefore necessary that the bone screws establish a rigid connection of the brace with the bone parts without having to exert an excessive force, through which the bone parts would otherwise be pressed onto the brace and placed under stress.

A fastening assembly allowing a screw to be screwed into the substructure at an angle with respect to the fixing element without increased force exertion and allowing an immovable connection free of play is disclosed in U.S. Pat. No. 4,388,921. This known fastening assembly comprises a bushing arranged in the bore of the fixing element, through which the screw can be passed for screwing the screw into the substructure. The bushing of this known fastening assembly is able to swivel in several spacial directions when seated in the bore. The bushing further comprises a seat for receiving the head of the screw. An inner surface of the bore and an outer surface of the bushing are formed to be about spherically curved, wherein a region of largest diameter of the inner surface of the bore is situated at the upper edge of the bore. By that the bushing can fall out of the bore as long as the screw is not screwed into the sub-structure. Therefore, the handling of this known fastening assembly is somewhat cumbersome because there are three parts, namely the fixing element, the screw and the bushing which must be held by hand when using the fastening assembly. In particular, in case that the fastening assembly must be fastened under a ceiling the bushing can fall out when manipulating the fixing elements and the screw. In medical applications there exists the risk that the bushing is lost in the human body.

The object of the present invention is therefore to provide a fastening assembly which is improved in terms of its handling properties.

SUMMARY OF THE INVENTION

This object is achieved according to the invention by a fastening assembly, comprising:
a fixing element to be fastened to a substructure, said fixing element having at least one bore;

at least one screw which can be passed through said at least one bore of said fixing element, and which can be screwed into said substructure, said screw having a shaft and a head;

at least one bushing arranged in said at least bore, through which said screw can be passed for screwing said screw into said substructure, said bushing being able to swivel in several spacial directions when seated in said bore, said bushing further comprising a seat for at least partially receiving at least a partial surface of said head of said screw, wherein an inner surface of said bore and an outer surface of said bushing are formed to be about spherically curved, such that a region of largest diameter of said inner surface and said outer surface is situated between an upper edge and a lower edge of said bore, wherein said bushing is loss-proof pressed in in said bore.

The fastening assembly according to the invention comprises a bushing which is received in the at least one bore of the fixing element and is mounted to be able to swivel or tilt in the bore in several spacial directions. Said in other words, the bushing can tilt or wobble in the bore. The screw to be driven into the substructure passes through this bushing in the bore. Due to the presence of the swivel-mounted bushing, the screw can pass through the fixing element at an angle in several directions, without the screw becoming clamped by the bushing, because the bushing then also adapts to the angle. Thus the longitudinal axis of the screw always remains substantially perpendicular to the upper and lower openings of the bushing. In this manner, the shaft of the screw does not catch on the upper or the lower edge of the bushing.

Also according to the invention, the bushing comprises a seat to at least partially receive a head of the screw. When drawing down the screw, the head at least partially engages with the bushing, for example it comes into contact with the bushing at least partially over a surface. When the screw head at least partially contacts or engages the seat of the bushing, the bushing becomes fixed in the bore. The screw head and the bushing then form a rigid immovable connection of the fixing element with the substructure. It is not necessary to apply excessive force to the screw to achieve the rigid connection of the fixing element to the substructure because a reliable anchoring of the screw in the fixing element is achieved through the engagement of the head with the bushing independent of the orientation of the screw with respect to the bore in the fixing element.

Further, according to the present invention, an inner surface of the bore and an outer surface of the bushing are formed to be about spherically curved, such that a region of largest diameter of the inner surface and the outer surface is situated between an upper edge of the bore and at a lower edge of the bore, wherein the bushing is loss-proof pressed in in the bore. This configuration of the fastening assembly has the effect that the bushing is retained in the bore so it cannot fall out because it is loss-proof pressed in in the bore. This simplifies the fastening of the fixing element to the substructure because the bushing does not need to be held by hand in the bore when applying the fixing element to the substructure.

In a preferred embodiment, a symmetry axis of the bushing can be swiveled, preferably over an entire azimuth angle of 360° in an angular range in the range of 0° to at least 45° with respect to a symmetry axis of the bore.

When the bushing is arranged in the bore to swivel or tilt within the mentioned solid angle range, the screw can be driven into the substructure without problem with the present fastening assembly in all cases where the screw intentionally or unintentionally is oriented at an angle with respect to the bore.

In a further preferred embodiment, the bushing is mounted directly in the bore.

The advantage is that the fastening assembly has a very simple construction, because further parts for mounting the bushing in the bore are not required. In this embodiment, the bore itself forms the bearing surface for the bushing.

In a further preferred embodiment, the bushing is received in form-locking manner in the bore.

The feature has the advantage that the bushing is carried in the bore in a manner substantially free of play due to the form-locking retainment.

In a further embodiment, the bushing is received to be swiveled in the bore through a bearing element, which can be fixed to the fixing element and which is arranged in the bore, and wherein in this case an inner surface of the bearing element is about spherically curved, such that a region of largest diameter of said inner surface and said outer surface is situated between an upper edge and a lower edge of the bearing element, wherein the bushing is loss-proof pressed in the bearing element.

This configuration has the advantage that conventional fixing elements can be subsequently equipped with a bushing according to the present invention. The bearing element can preferably be made together with the swivel bushing therein to form an inset, so that the bearing element with the bushing can be placed in the bore. For example, bearing elements in various sizes for corresponding bore diameters can be made available. The outer contour of the bearing element in the simplest case can be cylindrical so that the bearing element can be disposed in a conventional cylindrical bore in the fixing element. In household applications, this can be accomplished by the user himself or at most it could be necessary to enlarge the bore in the fixing element with a drill.

In a further preferred embodiment, the screw head and the seat of the bushing form a substantially form-locking connection.

With a form-locking configuration of the connection of the screw head with the bushing seat, a substantially play-free anchoring of the screw head in the bushing and therefore of the screw with the fixing element is achieved in constructively simple manner.

In a further preferred embodiment, the screw head and the bushing seat are formed to be conical and complementary to one another.

The feature has the advantage that the radially expanding sections act as engagement slopes through which the bushing is automatically tilted into the aligned position when the screw head sinks into the seat as the screw is being driven into the substructure. A further advantage is that the screw head and the bushing form a composite through which the anchoring of the screw in the fixing element is further improved when tightening the screw.

In a further preferred embodiment, an upper edge of the seat in the bushing is rounded.

This feature also provides an engagement slope which allows a self-alignment of the bushing with respect to the screw head, when the head comes into contact with the bushing. A clamping or blocking of the screw when being turned into the substructure is prevented.

In a further preferred embodiment, a periphery of the screw head is configured as a support surface, which in the tightened condition of the screw rests against a support surface of the bushing, formed to be approximately complimentary to the support surface of the head.

With this feature, the anchoring of the screw head with the bushing is improved in advantageous manner.

The bushing preferably has about the same height as the bore and the screw head preferably has about the same height as the seat in the bushing.

The feature has the advantage that the bushing does not project from the bore and the screw head remains completely sunk in the seating, so that the screw head, the bushing and the fixing element form a substantially edge-free uniform end surface in the region of the bore.

In a further preferred embodiment, the bushing is fabricated integrally of one piece of metal or synthetic material or has a metal body and the seat of the bushing can be at least partially coated with synthetic material.

Synthetic material has the advantage that the bushing can be radially elastically expanded to a large extent, so that the screw acquires an extensive frictional press fit in the seat when the screw head is sunk in the seat. At the same time, the seat is also firmly pressed against the bore or the bearing element, so that a completely immovable securement of the fixing element to the substructure is made possible. Such a completely immovable play-free press fit is however also achieved with a metal bushing and a conical configuration of the screw head and the bushing seat, when the bushing and the bore or the bearing element are configured to fit precisely to one another.

In a first preferred use, the fastening assembly according to the present invention is employed to secure a bone fracture in the human body, where the fixing element is a rigid plate or a rigid brace and the at least one screw is a bone screw. In this application in the medical field, the present fastening assembly is of particular advantage, because a stable play-free anchoring of a bone brace to the bone parts on either side of the fracture is achieved without drawing in the bone screws with excessive force.

In a further preferred use, the present fastening assembly is employed to mount an object on a wall, where the fixing element is a wall fixture, a profile or the like, or is employed for assembling furniture or the like, where the fixing element is an armature, a hinge, an angle or the like. Also in these applications, an immovable securement of a fixing element to a substructure, such as a wall or a ceiling, is made possible through the present fastening assembly, also when the screw or screws are applied at an angle to the substructure.

Further advantages can be taken from the following description and the attached drawings. It will be understood that the above mentioned features and those to be discussed below are applicable not only in the given combinations, but also in other combinations or taken alone without departing from the scope of the present invention.

Embodiments of the invention are illustrated in the drawings and will be described in detail in the following:

DETAILED DESCRIPTION OF PREFERRED EMBODIMENTS

Figure 1:
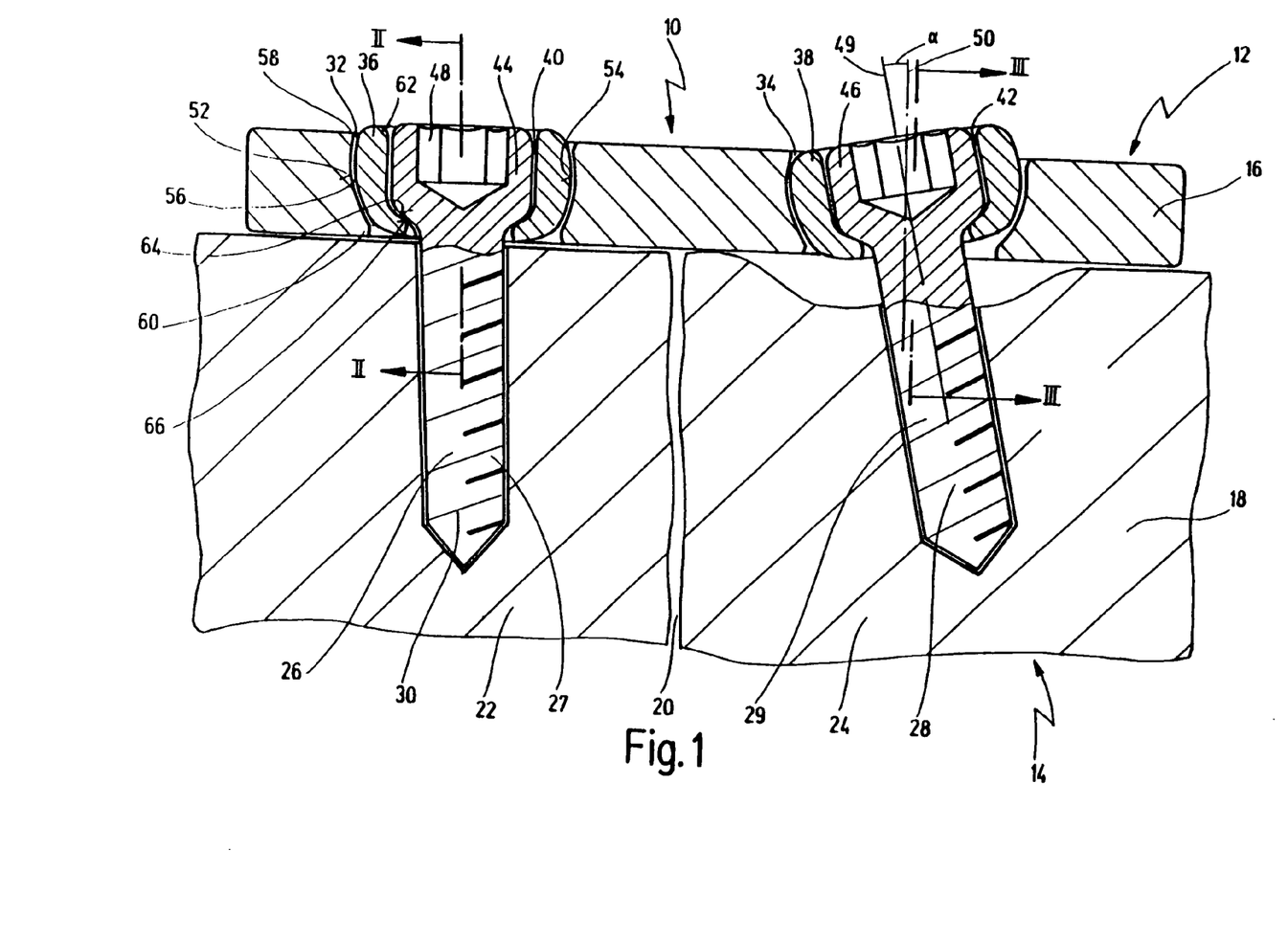
FIG. 1 shows a cross section of a fastening assembly according to the present invention in an application for example for securing a brace to a bone.
Figure 2:
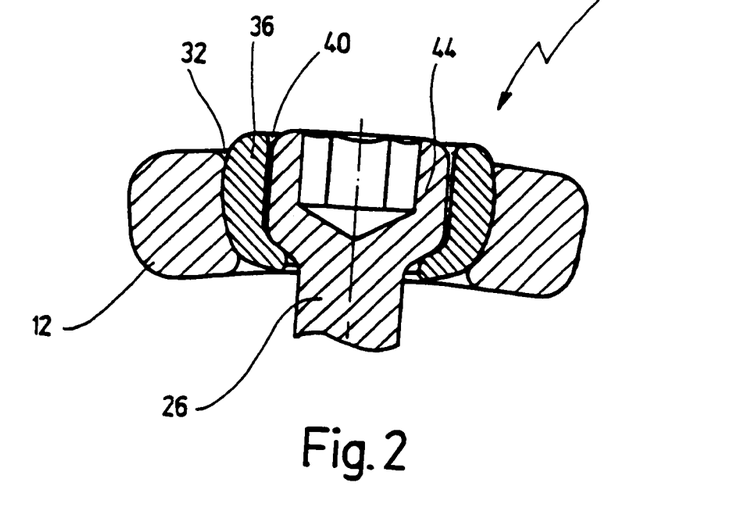
FIG. 2 shows a cross section through the fastening assembly in FIG. 1 along the line II-II.
Figure 3:
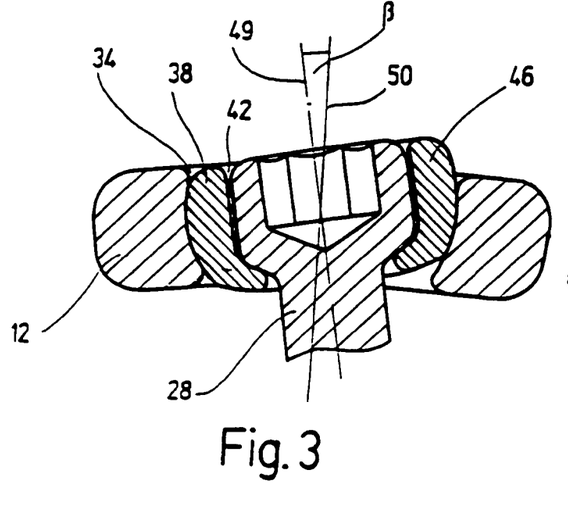
FIG. 3 shows a cross section through the fastening assembly in FIG. 1 along the line III-III.

FIGS. 1 to 3 illustrate a fastening assembly designated with the numeral 10 for fastening a fixing element 12 to a substructure 14.

In the illustrated embodiment, the fixing element 12 is a brace 16 in the form of an approximately rectangular elongated plate, which is secured to a bone 18 having a fracture 20. Two bone parts 22, 24 separated by the fracture 20 are fixed to one another by the brace 16 to heal the fracture 20. The brace 16 is fastened with a first screw 26 and a second screw 28 to the bone part 22 and the bone part 24, respectively. The first screw 26 and the second screw 28 are bone screws, each having a threading 30 formed on a shaft 27, 29 of the screw 26, 28. The threading 30 cuts a corresponding thread in the bone parts 22, 24 when turning the screw 26 or 28.

The brace 16 includes a first bore 32 and a second bore 34, where a first bushing 36 is received in the first bore 32 and a second bushing 34 in the second bushing 38. The first bushing 36 comprises a seat 40 and the second bushing 38 comprises a seat 42, which receives a head 44 of the screw 26 or, respectively, a head 46 of the screw 28. The head 44 of the screw 26 and the head 46 of the screw 28 each comprise an inner hexagon 48, which receives a hex head socket wrench in form-locking manner for screwing in and out the screws 26, 28.

The bushings 36, 38 are mounted in the bores 32, 34 to be able to swivel in several directions in the indicated embodiment in all spacial directions. This swiveling or tilting capability of the bushings 36, 38, however, is only present when the heads 44, 46 are not received in the seats 40, 42 of the bushings 36, 38. In the condition shown in FIGS. 1 to 3, the heads 44, 46 are disposed in the seats 40, 42 and the screws 26, 28 are screwed into the bone 18, such that the bushings 36, 38 are fixed. In the final mounted condition shown in FIGS. 1 to 3, the fixing element 12 is completely immovably connected to the substructure 14.

Figure 4:
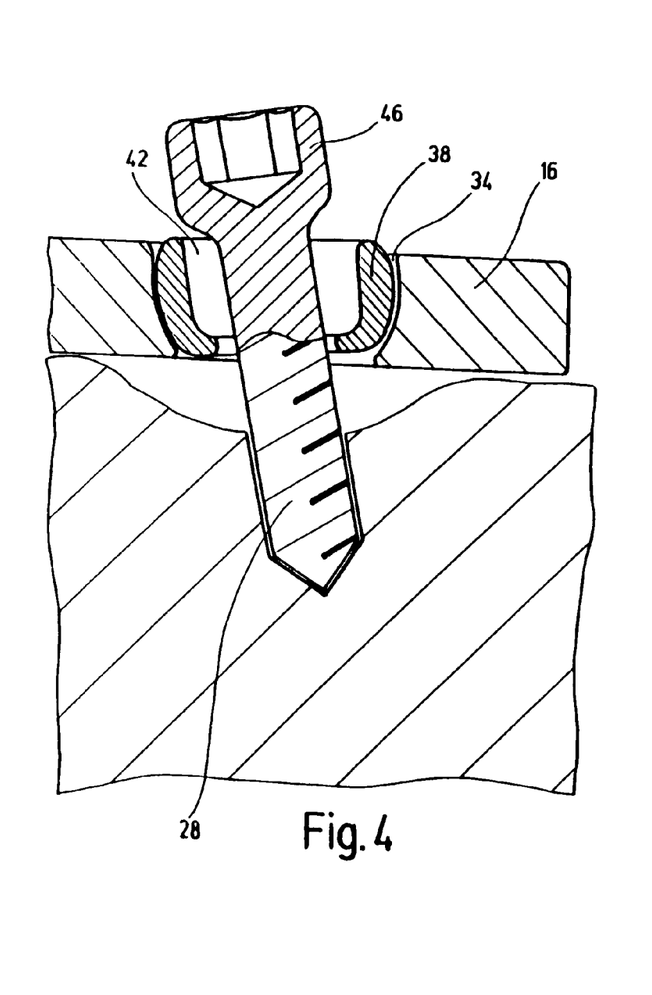
FIG. 4 shows a section of the fastening assembly in FIG. 1 in a representation corresponding to FIG. 1 illustrating the function of the fastening assembly when driving the screw into the substructure at a first stage.

The free swivel capability of the sleeve 36 or 38, however, exists as long the heads 44, 46 of the screws 26, 28 do not engage in the seat 40 of the bushing 36 or in the seat 42 of the bushing 38, as is illustrated in the example of the screw 28 and the bushing 38 in FIG. 4.

Figure 5:
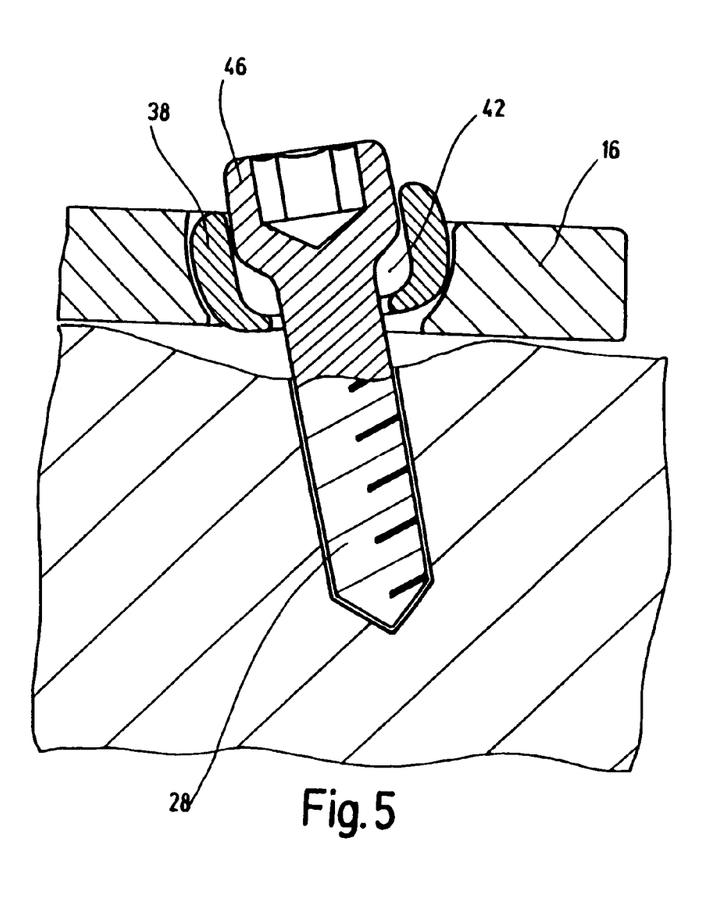
FIG. 5 shows an illustration according to FIG. 4 where the screw is driven into the substructure to an extent that the screw head just comes into contact with the bushing of the fastening assembly.

In the embodiment of FIGS. 1 to 3, the bushing 38 is tilted in the bore 34 of the brace 16 such that a symmetry axis 49 of the bushing 38 is inclined by an angle α (see FIG. 1) with respect to a symmetry axis 50 of the bore 34 with respect to the longitudinal axis of the brace 16 and is inclined in a direction transversely to the longitudinal axis of the brace 16 by an angle β (see FIG. 3). The free swivel capability of the bushing 28 has the effect that when the screw 28, as shown in FIGS. 1, 4 and 5 is screwed into the bone 18 at an angle, the bushing 38 is automatically positioned in the bore 34, such that the symmetry axis 49 of the bushing 38 coincides with the symmetry axis of the screw 28. Thus, a clamping of the screw 28 when being screwed into the bone 18 with the bushing 38 is avoided.

In the completely mounted condition, the head 46 of the screw 28 is received in form-locking manner in the seat 42 of the bushing 38. The form-locking engagement of the head 46 in the seat 42 of the bushing 38 is always automatically achieved by screwing in the screws 26 and 28, independent of whether the screw 28 is applied at an angle to the bone 18 or, as illustrated in the case of the screw 26, whether the screw 26 is applied perpendicularly to the bone 18.

When the screw 26 or 28 is completely inserted, the head 44 of the screw 26 or the head 46 of the screw 28 sits in a press-fit in the seat 40 or 42 of the bushing 36 or 38, and the bushing 36 and the bushing 38 are pressed against the wall of the bore 32 or 34.

Figure 7:
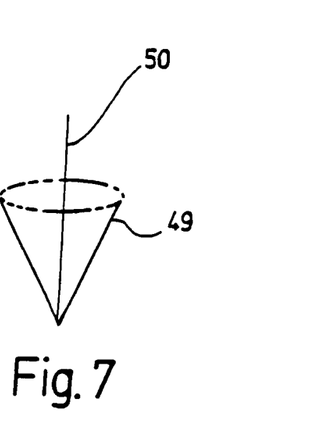
FIG. 7 shows a schematic illustration of the movability of the bushing about the symmetry axis of the bore of the fixing element.

The bushing 36 or the bushing 38 can be swiveled in the bore 32 or the bore 34 over the entire azimuth angle of 360° in an angular range of 0° to at least 45° (see FIG. 7). In FIG. 7, this is shown for a tilt angle of about 10°.

In the embodiment of FIGS. 1 to 3, the bushings 36, 38 are mounted directly in the bores 32, 34, namely the bushings 36, 38 are received in form-locking manner in the bores 32, 34. Due to the form-locking arrangement, the bushings 36, 38 are held to be non-releasable in the bores 32, 34. An inner surface 52 of the bore 32 of the brace 16 and an outer surface 54 of the bushing 36 are spherically curved for this purpose, where the inner surface 52 of the bore 32 is spherically concave and the outer surface 54 of the bushing 36 is spherically convex. A region 56 of the largest diameter of the inner surface 52 and the outer surface 54 then lies between an upper edge 58 of the bore 32 and a lower edge 60 of the bore 32. With this configuration, the bushing 36 is not releasable, however, can be freely pivoted in all spacial directions in the bore 32. The bushing 38 and the bore 34 have the corresponding configuration.

Further, an upper edge 62 of the bushing 36 is rounded, also on the bushing 38. A support surface 64 is formed on the head 44 of the screw 26 (as on the head 46 of the screw 28) in a peripheral region tapering radially downwardly. In the secured condition of the brace 16 shown in FIG. 1, the support surface 64 rests on an approximately complimentary support surface 66 of the bushing 36. On the whole, the head 44 lies completely sunk in the seat 40 of the bushing 36 to be flush in the seat 40 of the bushing 36. The counteracting, inclined support surfaces 64, 66 cause a slight expansion of the bushing 36 which improves the anchoring and pressing of the screw head 44 into the bushing 36.

As can be taken from FIGS. 1 to 3, the head 44 of the screw 26 has about the same height as the seat 40 in the bushing 36 and, in addition, the height of the bushing 36 is about the same as the bore 32, so that the upper edge 62 of the bushing 36 forms a substantially even surface with the upper side of the head 44 of the screw 26 and the upper side of the brace 16.

Figure 6:
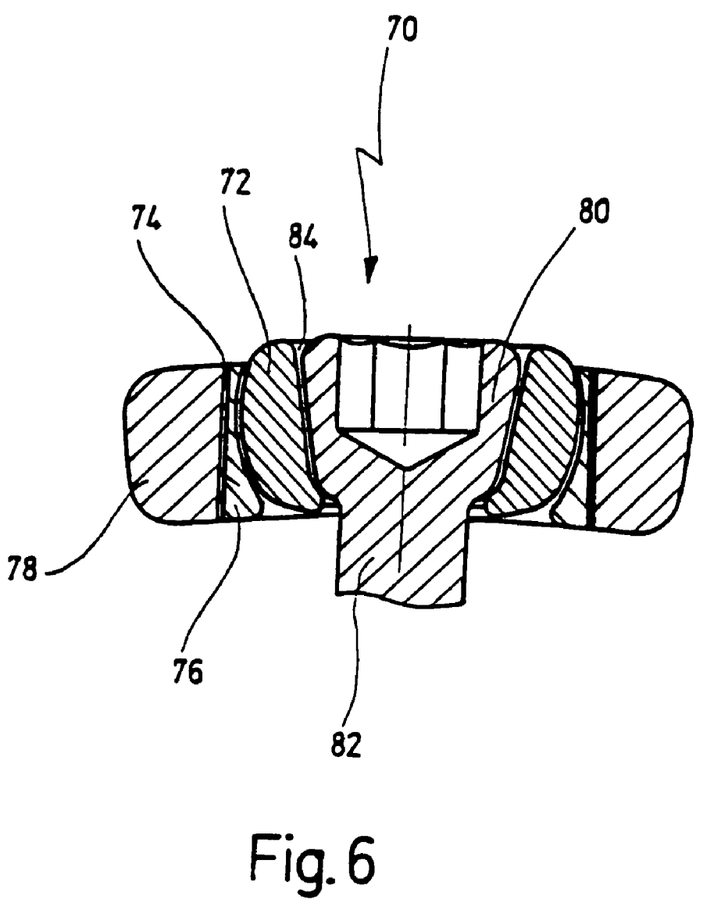
FIG. 6 shows a further embodiment of a fastening assembly in an illustration corresponding to FIG. 2.

FIG. 6 shows a further embodiment of a fastening assembly 70, which is modified in comparison to the fastening assembly 10 in that the bushing 72 in the bore 70 is swiveled mounted by means of a bearing element 76. The bearing element 76 is immovably received in the bore 74 of a fixing element 78. The bearing element 76 is configured for example to be slightly conical and is inserted from the bottom into the bore 74 of the fixing element 78. The bearing element 76 can be manufactured for example with the bushing 72 as an inset to be placed in the bore 74.

The bearing element 76 is adapted at its outer contour to the bore 74 and can be configured to be cylindrical instead of the truncated cone configuration shown in FIG. 6. In this case, a support ring can be provided at the lower edge of the bearing element 76, which engages with the edge of the bore 74 to prevent the bearing element 76 from being pushed out of the bore 74 in the upward direction.

The bushing 72 is form-locked and free to swivel in the bearing element 76 due to the corresponding shaping of the bearing element 76 and the bushing 72.

A further difference to the previous embodiment is that a head 80 of a screw 82 is formed to be conical and a seat 84 of the bushing 72 is also conical in compliment thereto. Compared to the previous embodiment, an improved anchoring of the head 80 in the bushing 84 is achieved with this configuration when the screw is firmly applied.

In the embodiment of FIG. 6 as well as the embodiment of FIGS. 1 to 3, the bushings 72, 36, 38 are made integrally in one piece of a metal or synthetic material. Alternatively, they have a metal body wherein the seats 40, 42, 48 in the respective bushings 36, 38, 72 are at least partially lined with a synthetic material.

Whereas the fastening assembly 10 was described for a special application in the medical field for fastening a brace 16 to a bone 18, it will be understood that such a fastening assembly can also be employed for technical applications, for example in the household for securing fixing elements such as plates, frames, angles, retainers, etc. to a wall or a ceiling.

What is claimed is:

1. A medical implant for use in the human body, comprising:
 a fixing element to be fastened to a bone, said fixing element having at least one bore;
 at least one bone screw which can be passed through said at least one bore of said fixing element, and which can be screwed into said bone, said bone screw having a shaft and a head;
 at least one bushing configured to be arranged in said at least one bore, through which said bone screw can be passed for screwing said bone screw into said bone, said bushing being able to swivel in several spacial directions when seated in said bore, said bushing further defining an opening therethrough, the opening having a first end and forming a seat extending through most of the bushing from the first end toward a second end of the opening for at least partially receiving at least a partial surface of said head of said bone screw, the seat comprising a distinct seat bottom at the second end of the opening;
 wherein an inner surface of said bore and an outer surface of said bushing are formed to be about spherically curved, such that a region of largest diameter of said inner surface and said outer surface is situated between an upper edge and a lower edge of said bore, wherein said bushing is loss-proof pressed in said bore;
 wherein an outer peripheral surface of the bone screw and an inner peripheral surface of the bushing form a threadless connection and substantially interlock with each other only at or only adjacent the seat bottom of the bushing to stop the head from passing completely through the bushing
 wherein the size of the opening adjacent the first end is larger than the size of the opening at the seat bottom.

2. The medical implant of claim 1, wherein a symmetry axis of said bushing can be swiveled preferably over an entire azimuth angle of 360° in an angular range of 0° to at least 45° with respect to a symmetry axis of said bore.

3. The medical implant of claim 1, wherein said bushing is mounted directly in said bore.

4. The medical implant of claim 1, wherein an upper edge of said seat at the first end of the opening of said bushing is rounded.

5. The medical implant of claim 1, wherein a periphery of said head of said screw is configured as a support surface, which in a tightened condition of said screw rests against the distinct seat bottom of said bushing formed to be approximately complimentary to said support surface of said head.

6. The medical implant of claim 1, wherein said bushing has approximately the same height as said bore, and wherein said head of said screw has approximately the same height as said seat of said bushing.

7. The medical implant of claim 1, wherein said bushing is integrally formed of metal or of synthetic material, or comprises a metal body with said seat of said bushing then being at least partially coated with synthetic material.

8. The medical implant of claim 1, wherein said fixing element is a rigid plate or a rigid brace and said at least one screw is a bone screw.

9. The medical implant of claim 1 wherein the interlock comprises engaging inclined surfaces of the head and the bushing relative to a central axis of the bushing, and the head is movable from a first position wherein the inclined surfaces initially contact each other to a second position wherein the head is inserted further into the seat.

10. The medical implant of claim 1, wherein the bushing comprises a continuous annular wall without any slots extending entirely radially through the wall.

11. The medical implant of claim 1 wherein the head of the bone screw is insertable into the opening of the bushing through the first end, but not through the second end.

12. A medical implant for use in the human body, comprising:
a fixing element to be fastened to a bone, said fixing element having at least one bore;
at least one bone screw which can be passed through said at least one bore of said fixing element, and which can be screwed into said bone, said bone screw having a shaft and a head;
at least one bushing configured to be arranged in said at least one bore, through which said bone screw can be passed for screwing said bone screw into said bone, said bushing further defining an opening therethrough, the opening having a first end and forming a seat extending through most of the bushing from the first end toward a second end of the opening for at least partially receiving at least a partial surface of said head of said bone screw, the seat comprising a distinct seat bottom at the second end of the opening;
wherein said bushing is received to be swiveled in said bore through a bearing element, which can be fixed to said fixing element and which is arranged in said bore, and wherein an inner surface of said bearing element and an outer surface of said bushing are formed to be about spherically curved, such that a region of largest diameter of said inner surface and said outer surface is situated between an upper edge and a lower edge of said bearing element, wherein said bushing is loss-proof pressed in said bearing element;
wherein an outer peripheral surface of the bone screw and an inner peripheral surface of the bushing form a threadless connection and substantially interlock with each other only at or only adjacent the seat bottom of the bushing to stop the head from passing completely through the bushing;
wherein the size of the opening adjacent the first end is larger than the size of the opening at the seat bottom.

13. The medical implant of claim 12 wherein the head of the bone screw is insertable into the opening of the bushing through the first end, but not through the second end.

* * * * *

UNITED STATES PATENT AND TRADEMARK OFFICE
CERTIFICATE OF CORRECTION

PATENT NO.       : 8,388,665 B2
APPLICATION NO.  : 11/804572
DATED            : March 5, 2013
INVENTOR(S)      : Roland Eberlein et al.

It is certified that error appears in the above-identified patent and that said Letters Patent is hereby corrected as shown below:

On the Title Page

(75) Inventors: Lothar Wilberg,     Delete "Bühlerianne"
Bühlerianne (DE)                        Insert -- Bühlertann --

Signed and Sealed this
Fifteenth Day of October, 2013

Teresa Stanek Rea
*Deputy Director of the United States Patent and Trademark Office*